United States Patent
Shah et al.

(10) Patent No.: US 8,257,719 B2
(45) Date of Patent: Sep. 4, 2012

(54) ORAL CARE LAYER AND RELATED METHOD OF MANUFACTURE

(75) Inventors: Kishore R. Shah, Bridgewater, NJ (US); Raynold M. Petrocelli, Grand Rapids, MI (US); Jeffrey J. Fisher, Ada, MI (US)

(73) Assignee: Ranir, LLC, Grand Rapids, MI (US)

( * ) Notice: Subject to any disclaimer, the term of this patent is extended or adjusted under 35 U.S.C. 154(b) by 1145 days.

(21) Appl. No.: 12/043,743

(22) Filed: Mar. 6, 2008

(65) Prior Publication Data

US 2008/0220032 A1  Sep. 11, 2008

Related U.S. Application Data

(60) Provisional application No. 60/893,296, filed on Mar. 6, 2007.

(51) Int. Cl.
*A61K 8/02* (2006.01)
*A61Q 11/00* (2006.01)

(52) U.S. Cl. .......................... 424/401; 424/53
(58) Field of Classification Search .................. None
See application file for complete search history.

(56) References Cited

U.S. PATENT DOCUMENTS

| | | | |
|---|---|---|---|
| 4,554,083 A | 11/1985 | Soldanski et al. | |
| 4,642,267 A | 2/1987 | Creasy et al. | |
| 5,718,886 A | 2/1998 | Pellico | |
| 5,844,013 A * | 12/1998 | Kenndoff et al. | 521/137 |
| 5,989,569 A | 11/1999 | Dirksing et al. | |
| 6,015,424 A * | 1/2000 | Rosenbluth et al. | 606/200 |
| 6,045,811 A | 4/2000 | Dirksing et al. | |
| 6,368,576 B1 | 4/2002 | Jensen et al. | |
| 6,419,905 B1 | 7/2002 | Alvarez Hernandez | |
| 7,138,458 B2 | 11/2006 | Cleary et al. | |
| 7,264,858 B2 * | 9/2007 | Belliveau et al. | 428/36.91 |
| 2001/0000801 A1 * | 5/2001 | Miller et al. | 623/1.11 |
| 2003/0152528 A1 * | 8/2003 | Singh et al. | 424/53 |
| 2005/0055044 A1 * | 3/2005 | Kangas | 606/194 |
| 2006/0099550 A1 | 5/2006 | Faasse et al. | |
| 2008/0255492 A1 * | 10/2008 | Truelsen et al. | 602/43 |

OTHER PUBLICATIONS

Tecophilic Solution Grade Technical Data Sheet, Nov. 2011, p. 1.*
Tecophilic Hydrogel Technical Data Sheet, Nov. 2011, p. 1.*
Technologies: Medical Urethanes downloaded from http://www.estane.com/technology/medical-urethanes.asp on Feb. 28, 2008.

(Continued)

*Primary Examiner* — Brian Gulledge
(74) *Attorney, Agent, or Firm* — Warner Norcross & Judd LLP (57) ABSTRACT

An oral care composition including a hydrophilic, aliphatic, polyether-based thermoplastic polyurethane, a glycol polymer, and a poly(N-vinyl lactam). These components form a tacky film having a thickness of about 1 mils to about 50 mils. A whitening agent, such as a peroxide, can be absorbed into the tacky film, and adapted to desorb from the tacky film to whiten teeth to which the film is joined. A method is also provided in which the components are extruded through a twin screw extruder and output to a die to produce the film. The whitening agent can be deposited on the film and absorbed by the film to form a relatively stable oral care composition including the whitening agent.

16 Claims, 4 Drawing Sheets

OTHER PUBLICATIONS

BASF Corporation Technical Bulletin, Pluronic F127 Surfactant Viscosity As a Function of Temperature & Concentration, 2006.

Desai, Suketu D./Blanchard, James, In Vitro Evaluation of Pluronic F127-Based Controlled-Release Ocular Delivery Systems for Pilocarpine, Journal of Pharmaceutical Sciences, pp. 226-230, vol. 87, No. 2, Feb. 1998.

Schmolka, Irving R., Artifical Skin I. Preparation and Properties of Pluronic F-127 Gels for Treatment of Burns, J. Biomed. Mater. Res., pp. 571-582, vol. 6 (1972).

Gu, Zhiyong/Alexandridis, Paschalis, Drying of Poloxamer Hydrogel Films, Journal of Pharmaceutical Sciences, pp. 1454-1470, vol. 93, No. 6, Jun. 2004.

\* cited by examiner

ORAL CARE LAYER AND RELATED METHOD OF MANUFACTURE

This application claims the benefit of priority to U.S. Provisional Patent Application 60/893,296, filed Mar. 6, 2007, which is hereby incorporated by reference.

BACKGROUND OF THE INVENTION

The present invention relates to oral care products, and more particularly to oral care layers, which can be used with oral care devices, and related methods of manufacture and use.

In the oral care industry, there are a variety of products designed to contact the teeth of a user to provide a desired effect. One example is a tooth whitening product in the form of a strip. The strip includes a whitening agent. To secure the strip to the teeth, an adhesive is joined with the strip in the form of a separate layer. To provide the desired whitening effect on the teeth, separate layers or regions of a whitening agent, such as hydrogen peroxide, are joined with the strip. Frequently, however, the adhesive and the whitening agent can be difficult to mix, can react with one another undesirably, or cannot provide the desired structural integrity.

In the cosmetic and medical fields, a certain type of composition, known as a hydrogel, can be used to contain and release active ingredients, absorb or release large amounts of water, and mimic biological tissues. These hydrogels generally are solutions or dispersions of water-soluble polymers within water, which yield a viscous or solid composition having a high water content.

Conventionally, hydrogels are manufactured by dispersing or dissolving polymers in water. Because the polymers are difficult to dissolve, large amounts of water are required. As a result, the water generally comprises more than 90% of finished gel composition. Frequently, it is desirable to have gels with a lower water content. Conventional techniques to achieve this lower water content include evaporation of the water or removal of a co-solvent, which yield the lower water content hydrogel. The issue with these techniques is that they still originate from a high solvent gel. Thus, extra time and resources are required to create the end product hydrogel.

SUMMARY OF THE INVENTION

The present invention provides an oral care composition and related manufacturing method that includes and utilizes very little water. The oral care composition can include a hydrophilic, aliphatic, polyether-based thermoplastic polyurethane; a hydrophilic polymer; and an oligomer, which form a film. The film readily absorbs or otherwise uptakes oral care agents and readily desorbs or releases those agents for direct application to surfaces to which the film is applied.

In one embodiment, the film can be incorporated into devices that apply oral care agents to the teeth and/or oral cavity of a user. Such oral care agents can include a variety of agents, including whitening agents, desensitizing agents and medicinal agents. For example, a whitening agent, such as a peroxide can be absorbed into the film. The whitening agent, however, can be readily desorbed from the film in the oral cavity. Accordingly, the film can apply the whitening agent to teeth, to which the film is applied, to provide a desired whitening effect.

In another embodiment, the hydrophilic polymer can be a poly(N-vinyl lactam), such as polyvinyl pyrolidone.

In yet another embodiment, the oligomer can be a glycol polymer, such as ethylene glycol.

The resulting film can have exceptional structural integrity and can be handled under tension without disintegrating during film production processes. The film can also have the following properties: a high mechanical strength when dry; a relatively high flexibility when dry; the ability to rapidly absorb compounds as well as systems, such as a solvent system; and the ability to maintain mechanical strength after having absorbed a compound and/or system.

In a further embodiment, the film can be included in a multi-layer construction by laminating multiple oral care layers. Due to the structural integrity of the film, the oral care layer can be drawn under tension through a laminating press, and readily laminated to construct oral care agent delivery devices.

In yet a further embodiment, the film can be manufactured by an extrusion process. In general, this process includes: melt processing through an extruder a mixture of the aliphatic, polyether-based thermoplastic polyurethane, the hydrophilic polymer, and the oligomer to form an extruded composition; and extruding the composition as a film of a desired thickness onto a suitable substrate. Optionally, after the film cools, the process can include depositing an oral care agent, such as a whitening agent, on or near the film and allowing the agent to absorb into the film. Further optionally, the latter deposition of the oral care agent on the film can prevent the oral care agent from being degraded substantially by the processing conditions used to make the film, and can potentially improve efficiency in manufacturing the oral care layer.

In yet another, further embodiment, the film can be manufactured by dissolving the aliphatic, polyether-based thermoplastic polyurethane, the hydrophilic polymer, and the oligomer in a suitable solvent, casting the mixture onto a backing or release liner, and allowing the solvent to evaporate, optionally with the assistance of heating, to produce a resultant film on the backing or release liner. Optionally, before or after the film sets, the process can include depositing an oral care agent, such as a whitening agent, on the film and allowing the agent to absorb into the film. Further optionally, the latter deposition of the oral care agent on the film can prevent the oral care agent from being degraded substantially by the processing conditions used to make the film, and can potentially improve efficiency in manufacturing the oral care layer.

These and other objects, advantages and features of the invention will be more readily understood and appreciated by reference to the detailed description of the invention and the drawings.

DETAILED DESCRIPTION OF THE INVENTION

I. Overview and Definitions

The present invention provides an oral care composition including a hydrophilic, aliphatic, polyether-based thermoplastic polyurethane; a hydrophilic polymer; and an oligomer, which form a film. The film readily absorbs oral care agents and readily desorbs those agents for direct application to surfaces to which the film is applied. Optionally, the film is tacky when wetted so that it readily adheres or joins with a surface that it contacts.

As used herein, the term "tacky," when referring to a film or layer, refers to a characteristic such that the film or layer is readily able to at least temporarily adhere to a surface to which the film or layer contacts, for example, a tooth surface. A tacky film or layer is also capable of adhering to the surface it contacts and supporting a remaining portion of the film or layer, so that the surface can be adequately treated by the film or layer or related agents for a period of time.

As used herein, the term "loaded" when referring to a film or layer, refers to a film that has been constructed from its primary ingredients to form the physical structure of the film, but in addition, has also been loaded with another compound, such as oral care agents and/or other optional components, by absorbing, joining or otherwise including those agents and/or components with and/or in the film.

As used herein, the term "dental product" refers to an appliance having or being modifiable to a configuration that facilitates placement of the product over at least a portion of a user's dental arch and/or oral tissue within the oral cavity. A dental product can include a front wall which engages the front surfaces of a user's teeth, a rear wall extending laterally from the front wall, either abruptly by at least one angle or non-abruptly by a curved part, configured to engage the rear surfaces of a user's teeth. The dental product can also include a trough between the front and rear walls. The dental product can also be configured so that a portion of it engages the incisal or occlusal portions of the user's teeth. Further, the dental product can be a dental wrap, constructed so that as a user wraps the product over the user's dental arch or oral tissue, the product's respective walls are formed.

As used herein, the term "aliphatic" refers to a group of organic compounds characterized by straight or branched chain arrangement of constituent carbon atoms.

As used herein, the term "hydrophilic," refers to polymers having a strong tendency to bind or absorb water, which results in swelling and formation of reversible swelling gels. A "swelling gel" is one that absorbs an amount of water greater than at least 100 weight % of its own weight when immersed in water.

As used herein, the term "polyether-based" refers to polymers that include or are derived from polyether, and the term "thermoplastic" refers to a high polymer that softens when exposed to heat and that returns to its original condition when cooled to room temperature.

As used herein, the term "polymer" refers to linear and branched polymers, cross-linked polymers, as well as copolymers (which optionally can be cross-linked), and thus block copolymers, alternating copolymers, random copolymers, and the like. Compounds referred to as "oligomers" herein are polymers having a molecular weight below about 1000 Da, optionally below about 800 Da.

As used herein, the term "hydrogel" refers to a network of polymers that are generally superabsorbant of water, but insoluble in water.

II. Oral Care Layer and Dental Products

The oral care layer ("OCL") according to the invention can include a hydrophilic, aliphatic, polyether-based thermoplastic polyurethane; a hydrophilic polymer; and an oligomer, which form a film. The following is a description of optional properties of OCLs, examples of OCL compositions; and OCLs included in dental products.

A. OCL Optional Properties

1. A balance of cohesion and adhesion (tack and peel adhesion) so that the composite product remains tightly adhered to teeth or oral tissue for oral treatment sessions, for example, teeth whitening sessions, ranging in duration from 1 minute to over 2 hours, without disintegrating or dissolving in the oral environment. The product also can be removable by peeling without leaving any adhesive mass on the teeth.

2. The properties of softness and flexibility for ease of application and conformability to teeth.

3. A rapid rate of absorption of oral care agents such as whitening and other agents.

4. The ability to bond to a woven or non-woven interlayer under certain laminating conditions.

5. The ability to store loaded oral care agents, for example, whitening agents, over a period of time with a high degree of stability.

B. OCL Compositions

The following are hydrophilic, aliphatic, polyether-based thermoplastic polyurethanes; hydrophilic polymers; oligomers; oral care agents and other components that may be used in one embodiment of the present invention.

1. Thermoplastic Polyurethanes

Examples of aliphatic thermoplastic polyurethanes (TPU) that can be used in the oral care layer can include hydrophilic, aliphatic, polyether-based thermoplastic polyurethanes. Suitable thermoplastic polyurethanes are those polymers available under the trade name "Tecophilic® Gel", which is commercially available from the Lubrizol Corporation of Cleveland, Ohio. Other optional TPUs include SP-80A-150 and SP-93A-100, also available from Lubrizol. In certain applications, hydrophobic TPUs, such as those available under the trade name "Tecoflex" or "Estane TPU," from Lubrizol, can also be useful.

The Tecophilic Gel can be provided as a resin form, as a dry powder, or as a dispersion system. The Tecophilic Gel comes in several polymer versions, including the TG-500 and TG 2000. The durometer of the TPU can range from 60D Shore through about 90A Shore. TG-500 can optionally have a durometer of 60D when dry, 80A when wet, and TG-2000 can optionally have a durometer of 60D when dry, as tested under ASTM Test D2240. The specific gravity of the TPU can range from 1.0 to about 1.25. TG-500 and TG-2000 can optionally have a specific gravity of 1.16, as tested under ASTM test D792.

The tensile strength of the TPU can range from about 1500 psi to about 0 psi. TG-500 optionally can have an ultimate tensile of about 1000 psi when dry and 250 psi when wet as tested under ASTM Test D412. TG-2000 can optionally have an ultimate tensile of about 750 psi when dry and can be a weak gel when wet as tested under ASTM Test D412. The TPU can also have a water pick up, measured as the amount of water loaded to the TPU as a percentage by weight of dry TPU, in a range having a lower end of about 100%, 200%, 300%, 400%, 500% or 600%, and an upper end of about 500%, 600%, 700%, 800%, 900%, 1000%, 1500%, or 2000%. TG-500 can optionally have a water pick up of about 500%, and TG-2000 can optionally have a water pick up of about 750% to about 900%, optionally about 2000%. The TPU can further have a melt index in g/10 minutes at a 2160 g load of about 5 to about 70, optionally about 50 at 150 degrees C. under ASTM Test D1238. TG-500 can optionally have a melt index in g/10 minutes at a 2160 g load of about 10 at 150 degrees C., while TG-2000 can optionally have a melt index in g/10 minutes at a 2160 g load of about 10 at 100 degrees C.

The TPUs noted herein can provide a hydrogel which can be reversibly dried. For example, the dried hydrogel can be reconstituted to its original state by adding water, after previous removal of all water and any other solvents. The TPUs can also have the property of being generally non-tacky before contact with water, but can become tacky upon being hydrated, for example, by contacting a moist surface like the surface of teeth in the mouth, and thus can adhere to the surface.

The TPUs can also be dissolved in a variety of solvents, such as IPA/water, ethanol/water, THF/water, and/or warm DMAC, or can be thermally processed by extrusion using single extruders or twin extruders, as discussed below. The TPU can also be melt processed using modified injection molding method to produce a consistent low-water hydrogel film. Further optionally, the TPUs can be very hydrophilic, but water-insoluble and can have a polarity which can contribute to adhesion when plasticized with an oligomer, such as an ethylene glycol polymer.

The TPUs used in the present invention can be present in the film (by percent weight of the film only) in a variety of ranges, for example, in a range having a lower end of about 1%, 2%, 3%, 4%, 5%, 10%, 12%, 15%, or 20%, and an upper end of about 10%, 12%, 15%, 20% or 25%. Further optionally, the TPU can be present in an amount of about 12% by weight of the dried film, or about 8.6% by weight of the loaded, finished film. In certain applications, the amount of TPU can be selected so that it forms an adequate hydrogel including an oral care agent solution, such as a peroxide solution, without rendering the finished film too plastic-like, and thus difficult to process.

2. Hydrophilic Polymers

Examples of hydrophilic polymers include poly(N-vinyl lactams), for example polyvinyl pyrolidone (PVP), available under the trade name Kollidon 90 F from BASF of Mount Olive, N.J., and specifically poly(N-vinyl 2-pyrrolidone). The average molecular weight of such polymers can range from about 100,000 to about 1,500,000, optionally about 500,000 to about 1,000,000. Optionally, the hydrophilic polymer is selected so that it will mix well, for example, homogeneously, with the oligomer, which can hydrogen bond to the hydrophilic polymer. Other optional hydrophilic polymers include cross-linked PVP, sodium carboxymethylcellulose, and cross-linked sodium carboxymethylcellulose.

The hydrophilic polymers used in the present invention can be present in the film (by percent weight of the film only) in a variety of ranges, for example, in a range having a lower end of about 30%, 40%, 50%, 60% or 70% and an upper end of about 50%, 60%, 70% or 80. Further optionally, the hydrophilic polymers can be present in an amount of about 58% by weight of the dried film, or about 42.3% by weight of the loaded, finished film. In certain applications, the amount of hydrophilic polymers can be selected so that they provide the finished film with sufficient body.

3. Oligomers

Examples of oligomers include glycol polymers, for example, a low molecular weight polyalkylene glycol, such as polyethylene glycol, having a molecular weight in the range of about 300 to about 600, optionally about 400 (for example, PEG 400, CARBOWAX® 400), ethylene glycol, propylene glycol, ether alcohol and the like. Other examples of oligomers include glycerine. Such oligomers can also serve as a plasticizer.

The oligomers used in the present invention can be present in the film (by percent weight of the film only) in a variety of ranges, for example, in a range having a lower end of about 10%, 20%, 30%, 40% or 50% and an upper end of about 20%, 30%, 40%, 50% or 60%. Further optionally, the hydrophilic polymers can be present in an amount of about 30% by weight of the dried film, or about 21.5% by weight of the loaded, finished film.

4. Oral Care Agents

Examples of oral care agents that can be used in the oral care layer can be whitening or bleaching agents, desensitizing agents, antimicrobials, anti-plaque agents, re-mineralizing agents, anti-tartar agents, mouth fresheners, anesthetics, fluorides, phosphates, stannates, nitrates, tooth-desensitizers, antibiotics, anti-inflammatory agents, enzymatic agents, nutritional supplements and the like. Specific whitening agents include, for example, hydrogen peroxide, carbamide peroxide, calcium peroxide, other peroxides, hypochlorites, peroxy acids, metal chlorites, chlorites, peroxidones, and/or PVP-peroxide complexes, which exert a dental bleaching activity on the teeth to which the composition is applied. Optionally, the oral care agent can be hydrogen peroxide present in a range of about 1% to about 20% by weight of the final, loaded hygrogel film. In one embodiment, the oral care agent can be present in the film in a range having a lower end of about 3%, 4%, 5%, 10% or 15% and an upper end of about 15%, 18%, 19%, or 20%. Further optionally, the oral care agent can be hydrogen peroxide present in an amount of about 6.4% by weight of the of the loaded, finished film.

5. Other Optional Components

The oral care layers also can optionally include other components provide desired properties. Examples of other components include: fillers, water, whitener stabilizers, such as EDTA, disodium EDTA, and salts thereof, citric acid and salts thereof, phosphoric acid and salts thereof, phenolphosphonic acid and salts thereof, gluconic acid and salts thereof, alkali metal pyrophosphates, alkali metal polyphosphates, and alkyl sulfates, neutralizing agents, such as sodium hydroxide and triethanolamine, alcohols, such as ethanol, and isopropyl alcohol, tetrahydrofuran, colorants, flavorants, such as vanilla, rose, menthol, mint, cinnamon, fruit and spices, sweeteners, such as saccharin, sodium saccharin and other artificial sweeteners, stabilizers, such as xanthum gum, preservatives, and the like. In one embodiment, the composition can include other components, each present in a range having a lower end of about 0.1%, 0.5%, 1%, 1.5%, 2%, 5% or 10% and an upper end of about 1%, 1.5%, 2%, 2%, 5%, 7%, 10%, 15%, 20%, 25%, 30%, 35% or 40%. Further optionally, the other components can be water present in an amount of about 19.50% to about 20.7%, sodium saccharin present in an amount of about 1.5%, citric acid present in an amount of about 1.14%, disodium EDTA present in an amount of about 1.08%, flavor present in about 0.8%, and xanthum gum present in an amount of about 0.75% by weight of the final, loaded film.

C. OCLs Incorporated into Dental Products

Figure 1:
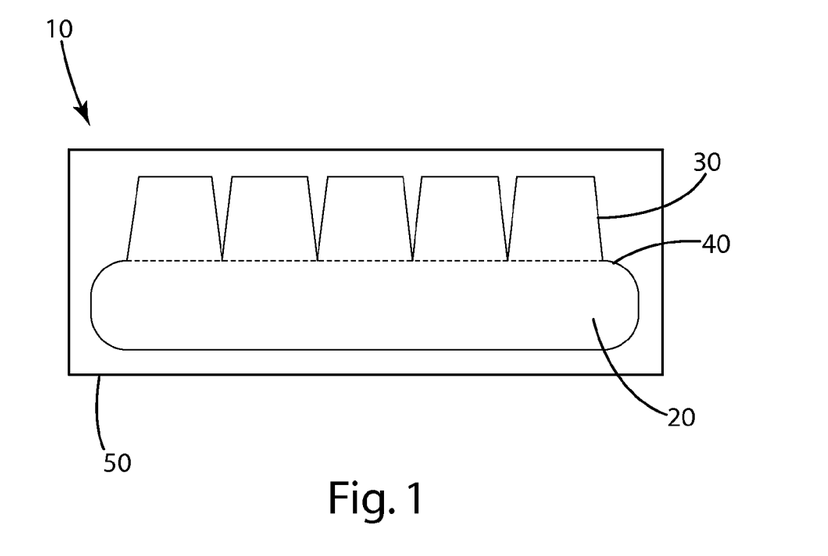
FIG. 1 is a perspective view of a dental product including the oral care layer of one embodiment before application to teeth.
Figure 2:
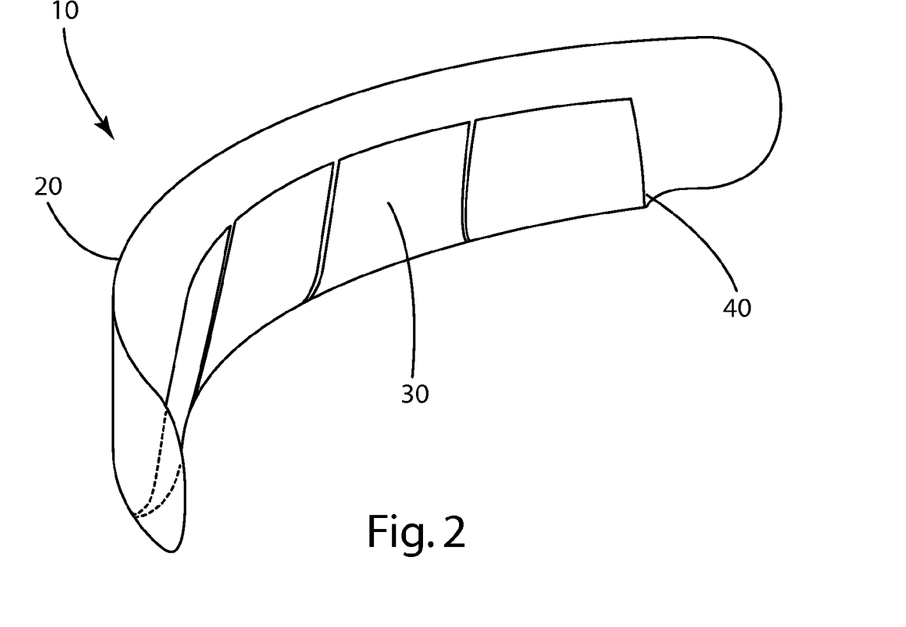
FIG. 2 is a perspective view of a dental product including the oral care layer as it would be configured when applied to teeth.

The oral care layer hydrogel film of the embodiments above can be included in a dental wrap construction. An example of a dental wrap construction, before and after application to teeth respectively, is illustrated in FIGS. 1 and 2. There, the dental wrap 10 includes a front wall 20, a rear wall 30, and a trough 40 having a "U" or "V" shape. The dental wrap can be joined with a substrate, such as a release liner 50 to which the film is joined until application to the teeth. This release liner can be constructed from silicone, polyethylene, high density polyethylene, low density polyethylene, ultra low density polyethylene, polypropylene, polytetrafluoroethylene, paraffin, wax, foil, paraffin, ethylene-vinyl acetate, ethylene-vinyl alcohol, polyvinyl chloride, polyurethane, polyester, polycarbonate, polyamide and polyesteramide, as the like. Optionally, the release liner can be about 1 mil to 100 mils, optionally about 20 mils to about 50 mils, and further optionally about 1.5 mils, and constructed from polyester as desired.

The thickness of the hydrogel film on the liner can be about 1 mil to about 50 mils, optionally about 5 mils to about 20 mils, further optionally about 6 mils to about 12 mils, and yet further optionally about 8 mils (not including the thickness of the liner).

In another embodiment, the hydrogel film can be included in a laminate having multiple layers. For example, the film may be joined with a structural portion that supports the film in a configuration similar to that in FIG. 2 before the dental product is applied to teeth. The film can also be joined with a dedicated adhesive layer as desired. An example of another dental product in which the hydrogel film can be included is disclosed in U.S. Patent Application Publication 2006/0099550 to Faasse, which is hereby incorporated by reference in its entirety.

III. Methods of Manufacturing Oral Care Layers

The OCL can be prepared in a variety of manners, including by blending and extruding and by solution casting. Several exemplary methods of making the OCL will now be described.

In one process, an OCL hydrogel film is manufactured by an extrusion process. In general, this process includes: melt processing through an extruder a mixture of the aliphatic, polyether-based thermoplastic polyurethane, the hydrophilic polymer, and the oligomer to form an extruded film composition; and extruding the composition as a film of a desired thickness onto a suitable substrate. Optionally, after the film cools, the process can include depositing a whitening agent, from about 1 to about 20 weight percent of the finished film, on the film, and allowing the whitening agent to absorb into the film.

Figure 3:
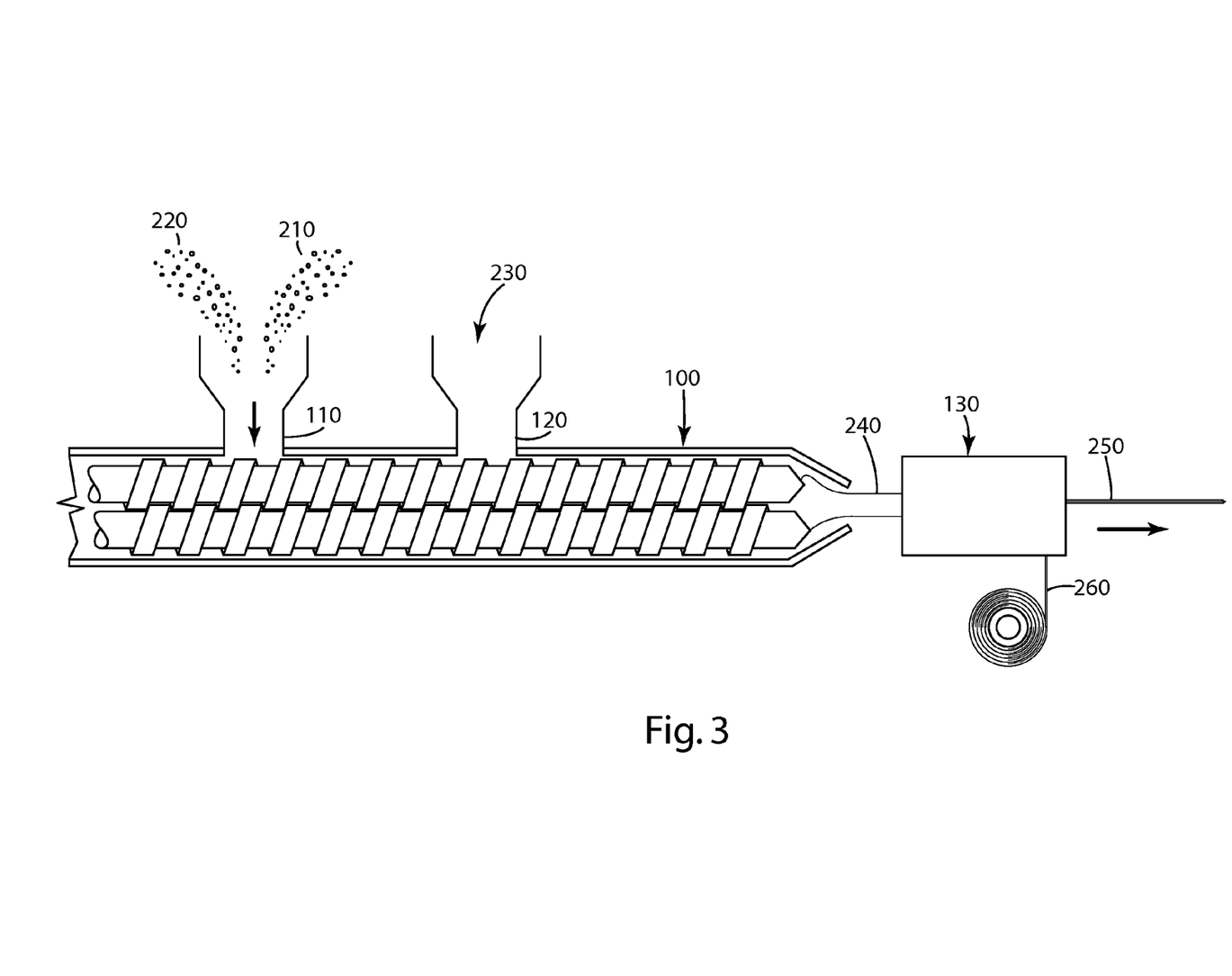
FIG. 3 is a schematic illustrating a process of manufacturing an oral care layer of one embodiment.

In a more particular process, the film can be processed through a twin screw extruder as illustrated in FIG. 3. There, a twin screw extruder 100 having an unheated section 110 and a heated section 120 is provided. TPU 210 is fed into a the twin screw extruder at the unheated section 110. A hydrophilic polymer 220 is also fed into the twin screw extruder at the unheated section 110. A glycol polymer 230 is fed into the twin screw extruder at the heated section 120. The mixture is combined in the twin screw extruder 100 to produce an extruded hydrogel composition 240. That extruded hydrogel composition 240 is fed to a die 130 to further extrude the extruded hydrogel composition 240 and form a hydrogel film 250 having a thickness of about 1 mil to about 50 mils, optionally about 8 mils. Optionally, the die can join a release liner 260 with the hydrogel film 250. The die itself can be opposing rollers, a single roller, a set of multiple rollers, a press, or any device capable of modifying a material to produce a sheet or strip or web of that material. A solution of water and an oral care agent, such as sodium peroxide, can be deposited on the film, for example by a slot die or Gardner knife coating other means, and allowed to absorb into the film. Due to this later addition of the oral care agent, the degradation of the agent in processing of the film is reduced or eliminated, and the process is rendered more efficient. Of course, other methods of producing the film can be used as desired.

Other components can be added as desired to the film as well. The finished oral care layer can then be cut into desired configurations suitable for placing the film in contact with a user's teeth. Alternatively, the finished oral care layer (with or without the release liner) can be incorporated into other dental products, such as the device in Faasse.

With the oral care layer being complete, it, along with the release liner can be placed in a pouch or packet that is further sealed form air and/or moisture. This pouch or packet can be placed in a package of multiple oral care layer pouches for further processing and distribution. A number of oral care layer pouches in a single package can provide a kit equal to the number of sessions required to achieve a desired effect with the kit, for example, whitening the teeth.

In an alternative process for manufacturing the oral care layer, the TPU, hydrophilic polymer, and oligomer can be prepared by solution. For example, the components can be mixed in a suitable solvent, such as a volatile solvent like ethanol or isopropyl alcohol or ethanol, at room temperature. The mixture can be cast on a substrate, such as a backing or release liner. A suitable release liner is a silicone treated 1.5 mil polyester release liner, for example, the liner available under the trade name Mylar®. Optionally, the mixture can be cast over the substrate with a casting knife or other suitable device. The film can be allowed to dry in an air circulating oven at about 70-85° C. for about 3 to about 6 minutes. The time of drying will depend on the thickness of the dried film, and, if included, the rate at which the solvent evaporates. If bubble entrapment occurs, the circulating air temperature can be raised, under which conditions the plasticized film sufficiently softens or fluidizes to allow the air bubbles to escape. After drying, the film on the liner can be removed and laid on a flat solid cool surface, which can act as a heat sink to cools the laminate to ambient temperature. An aqueous solution of an oral care agent, such as hydrogen peroxide, can be deposited on the layer by either a slot-die or a Gardner knife coating. The layer will absorb the aqueous solution. The surface of the film can be covered with a silicone coated release paper having release properties greater than that of the MYLAR® film. The film can then be stored in a moisture barrier package.

IV. Methods of Using Oral Treatment Compositions with Dental Products

The oral treatment composition can be used in a variety of ways. Several exemplary embodiments will now be described.

In a first embodiment, a dental product including the OCL loaded with a whitening agent as described above can be accessed by a user by removing the product from the pouch. The user can remove the release liner to access the OCL. The user can apply the dental product including the film to the upper or lower dental arch of the user, with the user wrapping the teeth with the product using the manual pressure of their digits over the front and rear surfaces of the desired teeth. After application of the pressure, the OCL or film remains in the shape of, and adhered to, the surfaces of the teeth of the user. This can be due to the tackiness of the film upon hydration when placed in contact with the teeth or generally within the oral cavity.

The dental product can be worn on teeth or other oral tissue, for example the gums, for several minutes to several hours, or some other pre-selected amount of time, depending, for example, on the particular oral care agent included with the film joined with the dental product. In one embodiment, a treatment session can last for about 10 to about 30 minutes.

Longer treatment sessions of about 30 minutes to about 2 hours are also contemplated. Treatment sessions can be repeated to obtain a desired degree of treatment. After the pre-selected amount of time, or after a desired amount of treatment, the dental product can be removed from the teeth or oral tissue. When used as a whitening dental product, the composition can be used once a day for 1 to 3 days to create visibly whiter teeth. For further whitening, the composition can be used once a day for 7 to 10 days. These treatment sessions can be repeated every six months or other frequency depending on the desired effect. In the case of bleaching devices, a clinical whitening effect has been observed after only 1 to 3 whitening sessions.

V. EXAMPLES

The following examples are supplied by way of example, not by limitation, to illustrate compositions and products of the present invention that can be useful for treating a person's teeth and/or oral tissue. Unless otherwise noted, percentages are percentage by weight, temperature is in degrees Celsius, and pressure is at or near atmospheric pressure.

A. Example 1

In this example, an oral care composition was prepared to form a film loaded with a whitening agent, the loaded film including the ingredients in Table I below. Of course, the ingredients and respective weight percentages can be altered to include those noted above as well.

TABLE I

Loaded Film

| Ingredient | % by Weight |
| --- | --- |
| TG-2000 | 8.6% |
| Polyvinylpyrolidone (Kollidon 90F) | 42.3% |
| Polyethylene glycol (PEG 400) | 21.5% |
| Hydrogen Peroxide | 6.4% |
| Sodium saccharin | 0.2% |
| EDTA | 0.1% |
| Sodium hydroxide | 0.1% |
| Polaxomer | 0.1% |
| Water | 20.7% |
| Total | 100.00% |

B. Example 2

Certain ingredients in Table 1 were melt processed to form a hydrogel film. Those ingredients were the TG-2000, the Polyvinylpyrolidone (Kollidon 90F); and Polyethylene glycol (PEG 400). These ingredients were present in the following amounts, based on the weight of the hydrogel film only: 12% TG-2000, 58% PVP and 30% PEG 400. The ingredients were processed on a 27 mm 40:1 L/D twin screw Leistritz extruder (available from American Leistritz Extruder Corporation of Somerville, N.J.) without a pre-compounding step. The extruder consisted of 12 heated zones, including the gear pump and die. The PVP and TG-2000 were top fed into an unheated feed section using loss weight screw hoppers. The PEG-400 was injected into the first heated zone immediately after the PVP and resin feed zone using a closed loop displacement pump system. It was found that the materials had adequate residence time to mix at output rates of between 20 and 40 lbs/hr.

The thickness, or gauge, of the film was easily controlled by adjusting the speeds of the take-up rolls and also by using a nip roll. The film did show a tendency to stick to the rolls, but the chiller temperature was increased to reduce the condensation on the roll and produce less sticking. The gauge was easily held at the target specification of 10 mils, and a sample was also made at 8 mils without difficulty (i.e. stretching or tearing). The target width of 8.5" was obtained using a 10" die while manipulating the speed of the first roll and the distance between the roll stack and the die.

After the film was created, the hydrogen peroxide and other ingredients in Table I above were added to the film by slot-die deposition, and allowed to absorb into the film. Excess ingredients which did not absorb were brushed off the film. The loaded film was covered with a release liner, and packaged in a moisture and air sealed pouch.

C. Example 3

In this example, the oral care composition including the ingredients of Table I was tested in vivo to determine whitening efficacy. The testing was performed on 10 individuals using the following procedure. First, the initial average whiteness of the top and bottom teeth for each individual was measured and recorded using an X-Rite ShadeVision System (available from X-Rite, Inc. of Grand Rapids, Mich.). Each individual wore dental wraps including the hydrogel film ingredients of Table I one day a week for seven days, for an average of 30 minutes per treatment session. The top and bottom teeth of each individual were then teeth were then measured with the ShadeVision System in its whitening value mode, and the average change in whiteness due to use of the composition was recorded as presented in FIG. 4.

Figure 4:
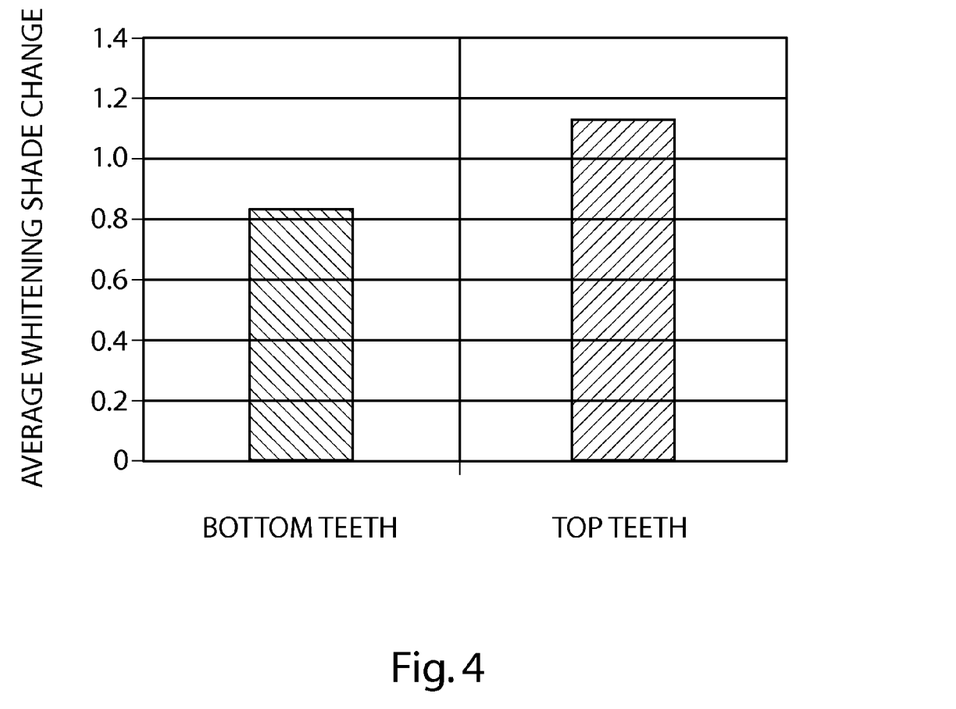
FIG. 4 is a graph illustrating the average whitening shade change provided by the oral care layer.

These results confirm that the oral care layer whitens teeth well, changing the average whitening shade as measured by the ShadeVision System by about 0.8 shades on the bottom teeth, and about 1.1 shades on the top teeth.

D. Example 4

In this example, the oral care composition including the ingredients of Table I was tested to determine the stability of the hydrogen peroxide present in the film over time. The oral care composition was included in various dental products packaged in air and moisture sealed pouches. Each individual pouch included 14 dental products (strips). The particular dental products in each pouch corresponded to dental products designed for the lower teeth (indicated as "lowers" in the legend in FIG. 5); dental products designed for upper teeth, but 1 treatment per day for 14 days (indicated as 1×14 in the legend in FIG. 5); and dental products designed for upper teeth, but 2 treatments per day for 7 days (indicated as 2×7 in the legend in FIG. 5).

Figure 5:
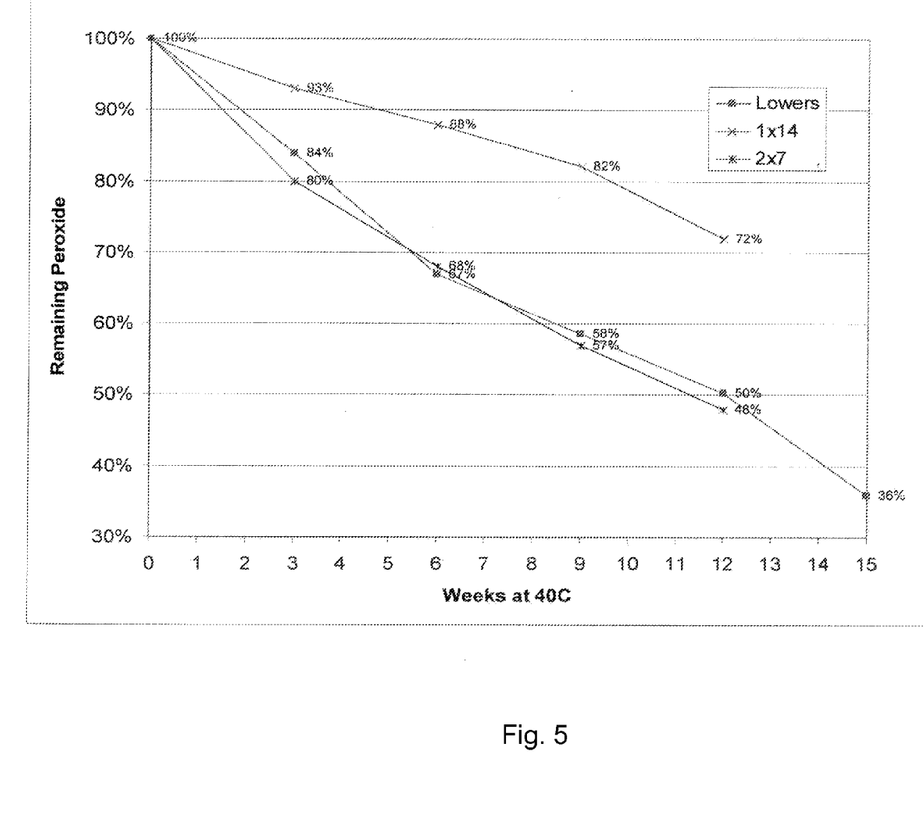
FIG. 5 is a graph illustrating the stability of the oral care layer over time.

The testing was performed over about 12 weeks, with the pouches maintained at 40 degrees Celsius. Specifically, two pouches from each group of the dental products noted above and shown in FIG. 5 were pulled and tested at three week intervals. Five dental products, each including the film of Table I, were analyzed for peroxide content as compared to the content when the pouch was first filled with the dental product. The results of this peroxide content is shown in FIG. 5 for the various tests. In addition, one dental product from each pouch was tested for solution pH, and one dental product from each pouch was tested with moist pH 3-6 paper. The titration results of each of these tests was recorded in milliliters per strip. This data was converted to pH units and recorded. The results of this test confirm that the oral care composition, when packaged, is quite stable in that the peroxide escapes the composition at a low rate. Thus, the respective dental products have relatively long shelf life.

The above and below descriptions are those of the preferred embodiments of the invention. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular. Any reference to "at least one of X, Y and Z" refers to only X, only Y, only Z, and any combination of X, Y, and Z.

The embodiments of the invention in which an exclusive property or privilege is claimed are defined as follows:

1. An oral care composition comprising:
a hydrophilic, aliphatic, polyether-based thermoplastic polyurethane material, present in an amount of about 1% to about 25% by weight of the composition,
a hydrophilic polymer present in an amount of about 40% to about 80% by weight of the composition; and
at least one of a glycol polymer and glycerine present in an amount of about 10% to about 40% by weight of the composition,
wherein the thermoplastic polyurethane material, the hydrophilic polymer and the at least one of a glycol polymer and glycerine are mixed together in a mixture to form a hydrogel film layer, the hydrogel included in a film layer having a thickness of about 1 mil to about 50 mils,
wherein the hydrogel film layer including the thermoplastic polyurethane material, the hydrophilic polymer and the at least one of a glycol polymer and glycerine is joined with a substrate layer,
wherein the substrate layer is adapted to wrap a plurality of teeth of a user so as to bring the hydrogel film layer into contact with the teeth,
wherein the hydrophilic, aliphatic, polyether-based thermoplastic polyurethane material becomes tacky when hydrated to promote adhesion of the hydrogel film layer to the teeth when the hydrogel film layer contacts a moist surface of the teeth.

2. The oral care composition of claim 1 wherein the film is formed by extruding the thermoplastic polyurethane material, the hydrophilic polymer and the at least one of a glycol polymer and glycerine through a twin screw extruder.

3. The oral care composition of claim 1 wherein the substrate layer is constructed from wax to form a wax substrate layer.

4. The oral care composition of claim 1 wherein the hydrogel film layer is joined with a structural portion to form a laminate.

5. The oral care composition of claim 3 wherein the at least one of a glycol polymer and glycerine is glycol polymer and the glycol polymer is polyethylene glycol present in an amount of about 30% by weight of the film.

6. The oral care composition of claim 4 wherein the hydrophilic polymer is polyvinyl pyrrolidone present in an amount of about 58% by weight of the film.

7. The oral care composition of claim 1 comprising a water-soluble oral care agent absorbed in the film.

8. The oral care composition of claim 7 wherein the water-soluble oral care agent is a whitening agent which is hydrogen peroxide.

9. The oral care composition of claim 1 comprising at least one of flavorants, sweeteners, colorants, preservatives, and stabilizers.

10. The oral care composition of claim 1 comprising an the oral care agent that is at least one of fluorides, phosphates, stannates, nitrates and peroxides.

11. An oral care composition comprising:
a hydrophilic, aliphatic, polyether-based thermoplastic polyurethane material having a hardness of Shore 60D when dry, and an equilibrium water content of about 500% to about 900%, based on weight of dry thermoplastic polyurethane material;
a glycol polymer; and
a poly(N-vinyl lactam), wherein the glycol polymer is hydrogen bonded to the a poly(N-vinyl lactam);
wherein the hydrophilic, aliphatic polyether-based thermoplastic polyurethane material, the glycol polymer, and the poly(N-vinyl lactam) are mixed together to form a hydrogel film layer having a thickness of about 1 mil to about 50 mils,
wherein the hydrogel film layer including the thermoplastic polyurethane material, the hydrophilic polymer and the glycol polymer is joined with a substrate layer,
wherein the substrate layer is adapted to wrap a plurality of teeth of a user so as to bring the hydrogel film into contact with the teeth,
wherein a peroxide is absorbed into the hydrogel film layer to form a loaded hydrogel film layer, but adapted to desorb from the loaded hydrogel film layer onto a surface of a user's teeth on which the loaded hydrogel film layer is placed by the user to impart a whitening effect on the teeth.

12. The oral care composition of claim 11 wherein the glycol polymer is polyethylene glycol present in an amount of about 15% to about 25% by weight of the loaded hydrogel film layer.

13. The oral care composition of claim 12 wherein the poly(N-vinyl lactam) is polyvinyl pyrrolidone present in an amount of about 35% to about 45% by weight of the loaded hydrogel film layer.

14. The oral care composition of claim 13 wherein the peroxide is hydrogen peroxide present in an amount of about 5% to about 10% by weight of the loaded hydrogel film layer.

15. The oral care composition of claim 11 wherein the substrate layer is constructed from wax to form a wax substrate layer, wherein the wax substrate layer and hydrogel film layer form a laminate.

16. The oral care composition of claim 15 wherein the hydrogel film layer is joined with a structural portion to form a laminate.

* * * * *